(12) United States Patent
Schmidt et al.

(10) Patent No.: US 8,529,446 B2
(45) Date of Patent: Sep. 10, 2013

(54) METHODS FOR DETERMINING PARAMETERS AND PLANNING CLINICAL STUDIES IN AUTOMATIC STUDY AND DATA MANAGEMENT SYSTEMS

(75) Inventors: Markus Schmidt, Nürnberg (DE); Siegfried Schneider, Erlangen (DE); Gudrun Zahlmann, Neumarkt (DE)

(73) Assignee: Siemens Aktiengesellschaft, Munich (DE)

( * ) Notice: Subject to any disclaimer, the term of this patent is extended or adjusted under 35 U.S.C. 154(b) by 1384 days.

(21) Appl. No.: 11/806,335

(22) Filed: May 31, 2007

(65) Prior Publication Data

US 2008/0194920 A1    Aug. 14, 2008

Related U.S. Application Data

(60) Provisional application No. 60/900,343, filed on Feb. 9, 2007.

(51) Int. Cl.
*A61B 5/00* (2006.01)
*A61B 5/05* (2006.01)
*G06K 9/62* (2006.01)
*G06F 17/00* (2006.01)
*G06N 5/00* (2006.01)
*G06N 5/02* (2006.01)

(52) U.S. Cl.
USPC ........... 600/300; 600/410; 382/155; 382/156; 382/157; 382/158; 706/45; 706/46

(58) Field of Classification Search
None
See application file for complete search history.

(56) References Cited

U.S. PATENT DOCUMENTS

| | | | | |
|---|---|---|---|---|
| 5,615,112 | A * | 3/1997 | Liu Sheng et al. | 1/1 |
| 5,871,019 | A * | 2/1999 | Belohlavek | 600/450 |
| 6,105,149 | A * | 8/2000 | Bonissone et al. | 714/26 |
| 6,819,790 | B2 * | 11/2004 | Suzuki et al. | 382/156 |
| 6,957,095 | B2 * | 10/2005 | Matsui | 600/407 |
| 7,054,823 | B1 * | 5/2006 | Briegs et al. | 705/2 |
| 7,526,132 | B2 * | 4/2009 | Koenig | 382/232 |
| 7,685,262 | B2 * | 3/2010 | Choubey et al. | 709/220 |
| 7,693,315 | B2 * | 4/2010 | Krishnan et al. | 382/128 |
| 7,860,287 | B2 * | 12/2010 | Zahlmann et al. | 382/128 |
| 7,983,933 | B2 * | 7/2011 | Karkanias et al. | 705/2 |
| 8,041,783 | B2 * | 10/2011 | Rahn et al. | 709/220 |
| 8,065,347 | B1 * | 11/2011 | DeMeyer et al. | 707/806 |
| 2004/0015079 | A1 * | 1/2004 | Berger et al. | 600/437 |
| 2004/0059597 | A1 * | 3/2004 | Tkaczyk et al. | 705/2 |
| 2004/0120580 | A1 * | 6/2004 | Sabol et al. | 382/224 |
| 2005/0182657 | A1 * | 8/2005 | Abraham-Fuchs et al. | 705/2 |
| 2005/0251011 | A1 * | 11/2005 | Zahlmann et al. | 600/407 |
| 2007/0192143 | A1 * | 8/2007 | Krishnan et al. | 705/3 |
| 2007/0276777 | A1 * | 11/2007 | Krishnan et al. | 706/46 |
| 2007/0292012 | A1 * | 12/2007 | Brandon et al. | 382/128 |
| 2009/0005669 | A1 * | 1/2009 | Schmidt et al. | 600/407 |
| 2009/0016579 | A1 * | 1/2009 | White et al. | 382/128 |

* cited by examiner

*Primary Examiner* — Bill Thomson
*Assistant Examiner* — Shirley Jian
(74) *Attorney, Agent, or Firm* — Harness, Dickey & Pierce, PLC

(57) ABSTRACT

In a method for determining a parameter in an automatic study and data management system, data is gathered in a knowledge database, and a parameter is determined based the data gathered in the knowledge database. The data is correlated to at least one of a configuration and implementation of a previous clinical study. The parameter is usable for configuring a future clinical study.

17 Claims, 1 Drawing Sheet

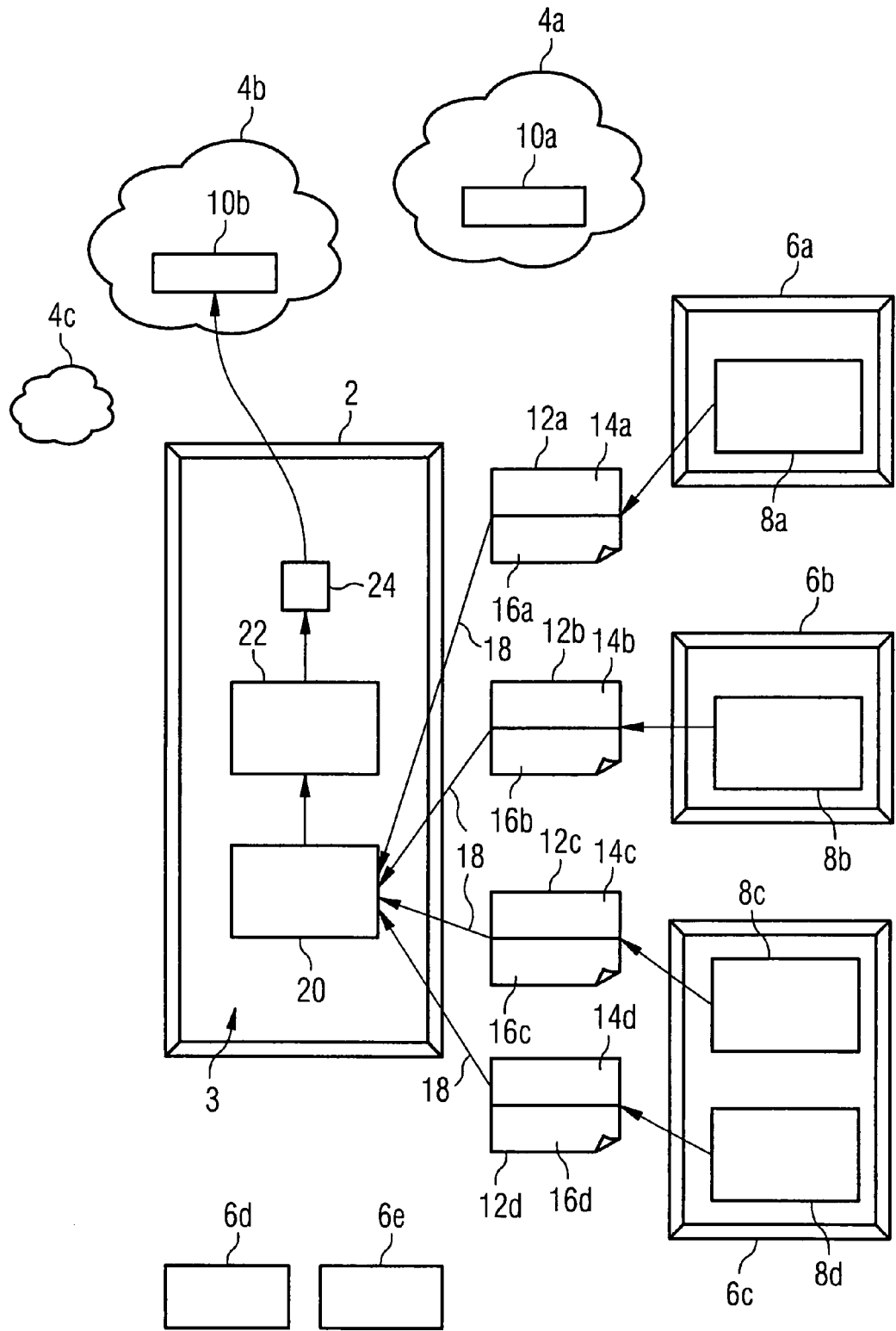

METHODS FOR DETERMINING PARAMETERS AND PLANNING CLINICAL STUDIES IN AUTOMATIC STUDY AND DATA MANAGEMENT SYSTEMS

PRIORITY STATEMENT

This non-provisional U.S. patent application claims priority under 35 U.S.C. §119(e) to U.S. provisional patent application Ser. No. 60/900,343, filed on Feb. 9, 2007, the entire contents of which is incorporated herein by reference.

BACKGROUND

Design, implementation and evaluation of clinical studies are complex ventures in which a large number of people and/or institutions are involved. A large volume of data is also produced. The administration complexity for this is immense. Conventionally, automatic study and data management systems are used as central support systems for designing, implementing and evaluating clinical studies.

In one example, all systems supplying data (e.g., imaging systems, electronic patient records, etc.) are integrated into a single study and data management system. The systems supplying data may be spread out over various sites and/or facilities, such as hospitals, doctors' practices, etc.

A conventional study and data management system is configured for each individual study in what is referred to as a setup process. This study-specific configuration is necessary to match relevant data flows from data sources and operating sequences to the requirements of a particular study. Data sources may be associated with the actual principal system (e.g., the study and data management system), and may include, for example, equipment at the clinics.

Results of the configuration performed during a setup process and/or the procedure of the setup process itself may be stored in a study protocol, referred to as Standard Operating Procedures (SOPs), and other documentation.

In adaptive clinical studies having modifiable procedures or courses, relevant configuration of the conventional study and data management system must (at least in part) have a variable system configuration, which is changeable during the course of the study.

Conventionally, the design of a clinical study (e.g., one which is to be implemented in the future) and the parameterization of a corresponding study and data management system are the task of a "principle investigator" or sponsor. The sponsor has access to its own experience with preceding clinical studies (e.g., already concluded or currently running clinical studies), and searches for additional required information for implementing the future study. Future studies, however, may be associated with considerable complexity.

SUMMARY

Example embodiments relate to methods and systems for ascertaining at least one parameter in an automatic study and data management system. The parameter may be determined for use in implementing, configuring or adapting one or more clinical studies.

At least one example embodiment provides a method and system for determining a parameter in an automatic study and/or data management system.

According to at least one example embodiment, data may be gathered in a knowledge database. The data may be correlated to a configuration and/or implementation of another clinical study (e.g., a preceding or previous clinical study). Based on the gathered data, a parameter for the clinical study may be determined automatically to enable a more fully automatic design of the clinical study.

At least one other example embodiment provides a method for automatically determining a parameter in a system for configuring a clinical study. According to at least this method, data correlated to at least one of a configuration and implementation of a first clinical study may be gathered in a knowledge database. The parameter may be automatically determined using the knowledge database. The parameter may be usable in configuring at least one of the first and at least one other clinical study.

According to at least some example embodiments, the data from preceding or previous clinical studies may include data regarding the implementation of one or more previous clinical studies, data from various facilities (or sites) involved in preceding studies, other parameters relevant to the study, etc. The data may be gathered in the knowledge database, and used to determine a parameter for the future clinical study. The gathered data may be proportional to the number of clinical studies preceding the future clinical study being planned. That is, for example, as the number of implemented clinical studies increases, the amount of data gathered may increase. Data gathered and stored in the knowledge base may also be referred to as gathered experience. In other words, for example, the gathered experience may be in the form of the data stored in the knowledge database.

The gathered experience may reflect experience with various investigators, data sources or the like. For example, the gathered experience may indicate a suitable (e.g., the most suitable or best) magnetic resonance (MR) sequence for a particular clinical study, reliability of data fields from different systems or investigators, etc. This gathered experience may improve the planning of a future clinical study and/or configuration of the automatic study and data management system for a future clinical study.

According to at least some example embodiments, the gathered experience may be of a technical nature, and may be gathered during configuration and/or implementation of a large number of studies (e.g., preceding or previous studies). The gathered experience may be stored in the knowledge database. This experience may also be in the form of data obtained from imaging modalities, result data from studies (outcomes) and/or quality data from images created in the course of the study. The data may be recorded and/or combined in the knowledge database. The knowledge database may grow with each implemented (e.g., each preceding) clinical study, and may be useful in generating proposals in the form of parameters for planning of studies and/or configuring study and data management systems. Such proposals and/or configurations may be re-encountered in study protocols for other studies.

Data correlated to preceding clinical studies may be gathered in the study and data management system. Parameters, stored in appropriately configured systems, may also be available to subsequent studies if the studies have comparable parameters.

In one example embodiment, the studies may be image-based studies. Image-based studies may require a relatively high level of planning, and their success may depend on a relatively large number of parameters. Example embodiments may take into account and/or consider all or substantially all of these factors in planning future studies.

Gathered data may include image data, metadata correlated to the image data, study results, etc., and/or some combination thereof. Image data and associated metadata (e.g., picture parameters, modality, etc.) may produce relatively large volumes of data, which example embodiments may render manageable such that the image data and metadata may be used in planning and/or modifying studies.

A determined parameter may be a parameter correlated to a study protocol and/or a standard operating procedure (SOP) for one or more clinical studies. Example embodiments may thus have a more direct effect on studies.

A parameter may be determined iteratively or repeatedly during the implementation of the future study. As a result, information in the knowledge database, which may change during the study, may be used (e.g., in real time or as close to real time as desired) for determining the parameter. In this case, the parameter may be used to modify the behavior and/or configuration of the automatic study and data management system, to implement and/or configure a future clinical study.

The parameter may be provided as a consultancy service for a design of future studies. According to at least one example embodiment, the parameter may not be used directly in the study, but instead as a consultancy service for the design.

BRIEF DESCRIPTION OF THE DRAWINGS

The present invention will now be described with regard to example embodiments shown in the drawings, in which:

FIG. 1 shows a block diagram illustrating an automatic clinical study data evaluation system according to an example embodiment.

DETAILED DESCRIPTION OF EXAMPLE EMBODIMENTS

Various example embodiments of the present invention will now be described more fully with reference to the accompanying drawings in which some example embodiments of the invention are shown. Detailed illustrative embodiments of the present invention are disclosed herein. However, specific structural and functional details disclosed herein are merely representative for purposes of describing example embodiments of the present invention. This invention may, however, may be embodied in many alternate forms and should not be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments of the invention to the particular forms disclosed, but on the contrary, example embodiments of the invention are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or" includes any and all combinations of one or more of the associated listed items.

The terminology used herein is for the purpose of describing particular embodiments only and is not intended to be limiting of example embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the FIGURE.

According to at least one example embodiment, a central station (e.g., a sponsor) may implement a relatively large number of clinical studies (e.g., different clinical studies) at different execution stations (or sites, such as, clinics, doctor's offices, etc.) over a period of time. According to at least one example embodiment, all or substantially all studies may be image-based (e.g., producing MRI image data, X-ray image data, etc.), and thus, all or substantially all implementing institutions (or sites) may include magnetic resonance (MR) or X-ray modalities.

FIG. 1 is a block diagram illustrating an example embodiment of an automatic clinical study and data evaluation system. The system of FIG. 1 may be used, for example, to implement and/or plan a clinical study with an automatic study and data management system.

Referring to FIG. 1, the study data evaluation system may include a study management system 2, which may further include a data management system 3. The study management system 2 may be used to implement a clinical study 4a at a plurality of (e.g., three) clinics 6a-6c. As an example, each of clinics 6a and 6b may include a respective imaging modality 8a and 8b, and clinic 6c may include two modalities 8c and 8d. The clinical study 4a may be based on a study protocol 10a. Study protocol 10a may include, for example, a standard operating procedure (SOP), steps to be implemented within the context of the study 4a, etc.

Based on the instructions in the study protocol 10a, the clinics 6a-6c use the imaging modalities 8a-8d to examine patients (not shown), and produce images 12a-12d associated with the examined patients. Clinics 6a-6c may configure their MR modalities based on or according to requirements of the study protocol 10a, and set MR sequences accordingly. In this example, images 12a-12d contain respective actual image data 14a-14d and respective metadata 16a-16d associated with each image 12a-12d. However, any or all images 12a-12d may include only image data 14a-14d or only metadata 16a-16d.

In one example, the metadata 16a-16d may be header data for the image data 14a-14d. In this example, the metadata 16a-16d may contain information about the respective modalities 8a-8d, the clinics 6a-6c, a patient, additional picture parameters, etc. and/or any combination thereof. The actual image data 14a-14d may be pre-processed by respective modalities 8a-8d.

Referring still to FIG. 1, all or substantially all images 12a-12d may be transmitted from the clinics 6a-6c to the data management system 3 within the study management system 2 as indicated by the arrows 18 in FIG. 1. The images 12a-12d may be received by a central support system 20 within the data management system 3. The data management system 3 may gather, store and/or evaluate the transmitted image data 14a-14d and/or the metadata 16a-16d.

According to at least one example embodiment, the central station or sponsor may use the study management system 2 to gather all or substantially all study-related data in a data management system 3, plan and/or manage clinical studies based on the stored data.

Referring back to FIG. 1, data describing the configuration of the modalities together with the analysis results from the study 4a may be output from the central support system 20 to the knowledge database 22.

The knowledge database 22 may store all or substantially all data correlated to the clinical study 4a. Based on the data stored in the knowledge database 22, the study management system 2 may ascertain, generate or determine a parameter 24, usable in the same and/or another (e.g., newly implementable or future) clinical study 4b and/or study protocol 10b.

Using suitable algorithms, analysis results from the clinical study 4a may be correlated to configuration settings of MR modalities in any or all of the clinics 6a-6c.

According to at least one example embodiment, the study management system 2 may determine a parameter as follows. This example will be described with regard to modalities 8c and 8d at clinic 6c, however, the number and type of modalities and clinics should not be considered limiting. The method described herein is equally applicable to other modalities and clinics set forth herein and those well-known in the art.

As one example, the modality 8c at clinic 6c (e.g., an MR modality) may be used for routine imaging during the clinical study 4a. During the clinical study 4a, various sequences may be used in the modality 8c. In this case, the metadata 16c may contain, for example, use and error statistics for the modality 8c and study results including, for example, diagnosis information associated with the image data 14c.

Relevant information for the image data 14d may also be included in the metadata 16d. Modality 8d may be, for example, an MR modality. Because the use and error statistics for modality 8c in the database 22 may be more favorable than those for the modality 8d, the study management system 2 may generate a parameter 24 indicating that the future clinical study 4b should be implemented based on modality 8c. Thus, information extracted from the preceding study 4a may be used in the design of the clinical study 4b to be implemented in future.

When implementing the future study 4b, the study management system 2 may be configured with parameter 24 and may fetch (or obtain) appropriate image data from (e.g., only from) modality 8c as opposed to modality 8d. Images produced incorrectly by the clinic 6c using the modality 8d may be identified (e.g., from associated header data for example) and rejected. That is, for example, the study management system 2 may selectively obtain data from particular modalities and/or clinics based on the one or more determined parameters.

The clinical study 4b may involve participation by other clinics, for example, clinics 6d and 6e. As above, the clinics 6a-6d may gather MR image data and supply the gathered MR image data to the data management system 3 at the central station. As above, data sub-records associated therewith may be transferred to a knowledge database 22.

Across each of clinical studies 4a and 4b, the study management system 2 may use algorithms to evaluate and configure configuration settings of MR modalities at the clinics 6a-6e. In this example, the configuration settings may be set relative to successful data collection. When planning a (e.g., future or new) clinical study 4c, the knowledge database 22 may be accessed to ascertain or determine settings (e.g., optimum settings) for MR modalities at any or all of the clinics 6a-6e. This may assist in the creation of parts or portions of the study protocol 10c for the clinical study 4c, for example, those portions which relate to the capture of image data.

Although example embodiments have been described as being used to implement a clinical study, it will be understood that similar methods and apparatuses may be used to adaptively configure a current clinical study. That is, for example, during a current clinical the study management system 2 may receive data from one or more clinics, evaluate the received data to generate one or more parameters as described above, and adaptively configure or re-configure the current clinical study based on the determined parameters. According to at least one example embodiment, a parameter may be indicative of at least one characteristic of a configuration of a clinical study. A characteristic of a configuration of a clinical study may be, for example, clinics and/or modalities from which to gather data for gathering data at the study and data management system 2.

Methods according to example embodiments may be machine implemented via one or more computers or processors. In addition, the systems discussed herein may be embodied in the form of one or more computers configured to carry out methods described herein.

Example embodiments may also be implemented, in software, for example, as any suitable computer program. For example, a program in accordance with one or more example embodiments of the present invention may be a computer program product causing a computer to execute one or more of the example methods described herein: a method for determining a parameter in a system for implementing a future clinical study.

The computer program product may include a computer-readable medium having computer program logic or code portions embodied thereon for enabling a processor of the apparatus to perform one or more functions in accordance with one or more of the example methodologies described above. The computer program logic may thus cause the processor to perform one or more of the example methodologies, or one or more functions of a given methodology described herein.

The computer-readable medium may be a built-in medium installed inside a computer main body or removable medium arranged so that it can be separated from the computer main body. Examples of the built-in medium include, but are not limited to, rewriteable non-volatile memories, such as RAMs, ROMs, flash memories, and hard disks. Examples of a removable medium may include, but are not limited to, optical storage media such as CD-ROMs and DVDs; magneto-optical storage media such as MOs; magnetism storage media such as floppy disks (trademark), cassette tapes, and removable hard disks; media with a built-in rewriteable non-volatile memory such as memory cards; and media with a built-in ROM, such as ROM cassettes.

These programs may also be provided in the form of an externally supplied propagated signal and/or a computer data signal (e.g., wireless or terrestrial) embodied in a carrier wave. The computer data signal embodying one or more instructions or functions of an example methodology may be carried on a carrier wave for transmission and/or reception by an entity that executes the instructions or functions of the example methodology. For example, the functions or instructions of the example embodiments may be implemented by processing one or more code segments of the carrier wave, for example, in a computer, where instructions or functions may be executed for determining a parameter in a system for implementing a future clinical study, in accordance with example embodiments described herein.

Further, such programs, when recorded on computer-readable storage media, may be readily stored and distributed. The storage medium, as it is read by a computer, may enable the methods and/or apparatuses, in accordance with the example embodiments described herein.

Example embodiments being thus described, it will be obvious that the same may be varied in many ways. For example, the methods according to example embodiments of the present invention may be implemented in hardware and/or software. The hardware/software implementations may include a combination of processor(s) and article(s) of manufacture. The article(s) of manufacture may further include storage media and executable computer program(s), for example, a computer program product stored on a computer readable medium.

The executable computer program(s) may include the instructions to perform the described operations or functions. The computer executable program(s) may also be provided as part of externally supplied propagated signal(s). Such variations are not to be regarded as departure from the spirit and scope of the example embodiments, and all such modifications as would be obvious to one skilled in the art are intended to be included within the scope of the following claims.

The present invention being thus described, it will be obvious that the same may be varied in many ways. Such variations are not to be regarded as a departure from the invention, and all such modifications are intended to be included within the scope of the present invention.

We claim:

1. A method of planning a clinical study with a study and data management system, the method comprising:
    gathering, in a knowledge database of the study and data management system at least partially executed by a processor, data correlated to at least a first clinical study, the first clinical study being an image-based study with a plurality of images being acquired by a plurality of imaging modalities, wherein
        the gathered data includes image data, metadata and image study results, the metadata being associated with the image data and containing configuration settings of at least one of the imaging modalities, the configuration settings being settings of the imaging modalities utilized when acquiring the associated image data during the first clinical study;
    correlating the image study results to the configuration settings of the imaging modalities; and
    automatically determining optimum configuration settings for imaging modalities to be used in a future clinical image study by accessing the knowledge database.

2. The method of claim 1, wherein the determined configuration settings are associated with at least one of a study protocol and a standard operating procedure for the future clinical image study.

3. The method of claim 1, wherein the configuration settings are determined iteratively during implementation of the future clinical image study.

4. The method of claim 1, further comprising:
    implementing the future clinical image study using the determined configuration settings.

5. The method of claim 4, wherein the configuration settings are determined iteratively during the implementation of the future clinical image study.

6. The method of claim 1, further comprising:
    designing the future clinical image study based at least in part on the configuration settings.

7. The method of claim 6, further comprising:
    implementing the designed future clinical image study.

8. The method of claim 1, wherein the first clinical study is a previous clinical study.

9. A method for automatically planning a clinical study, the method comprising:
    gathering, in a knowledge database of a clinical study configuration system at least partially executed on a processor, data correlated to a previous clinical study, the previous clinical study being an image-based study with a plurality of images being acquired by a plurality of imaging modalities, wherein
        the gathered data includes image data, metadata and image study results, the metadata being associated with the image data and containing configuration settings of at least one of the imaging modalities, the configuration settings being settings of the imaging modalities utilized when acquiring the associated image data during the first clinical study;
    correlating the image study results to the configuration settings of the imaging modalities;
    determining optimum configuration settings for imaging modalities to be used in a future clinical image study by accessing the knowledge database; and
    configuring the future clinical image study based on the determined configuration settings.

10. The method of claim 9, wherein the configuration settings are associated with at least one of a study protocol and a standard operating procedure for the future clinical image study.

11. The method of claim 9, further comprising:
    implementing the configured future clinical image study.

12. A computer readable medium storing computer program instructions executable by a computer, when executed by the computer, the instructions cause the computer to execute a method for automatically determining a configuration settings in a system for configuring a clinical study, the method comprising:
    gathering, in a knowledge database of a study and data management system, data correlated to at least a first clinical study, the first clinical study being an image-based study with a plurality of images being acquired by a plurality of imaging modalities, wherein
        the gathered data includes image data, metadata and image study results, the metadata being associated with the image data and containing configuration settings of at least one of the imaging modalities, the configuration settings being settings of the imaging modalities utilized when acquiring the associated image data during the first clinical study;
    correlating the image study results to the configuration settings of the imaging modalities; and
    automatically determining optimum configuration settings for imaging modalities to be used in a future clinical image study by accessing the knowledge database.

13. The computer readable medium of claim 12, wherein the method further comprises:
    designing the future clinical image study based at least in part on the configuration settings.

14. The computer readable medium of claim 12, wherein the method further comprises:
    implementing the designed future clinical image study.

15. The computer readable medium of claim 12, wherein the first clinical study is a previous clinical study.

16. A computer readable medium storing computer program instructions executable by a computer, when executed by the computer, the instructions cause the computer to execute a method for automatically planning a clinical study using an automatic data and study management system, the method comprising:

gathering, in a knowledge database, data correlated to a previous clinical study, the previous clinical study being an image-based study with a plurality of images being acquired by a plurality of imaging modalities, wherein the data gathered in the knowledge database includes image data, metadata and image study results, the metadata being associated with the image data and containing configuration settings of at least one of the imaging modalities, the configuration settings being settings of the imaging modalities utilized when acquiring the associated image data during the first clinical study;

correlating the image study results to the configuration settings of the imaging modalities;

determining optimum configuration settings for imaging modalities to be used in a future clinical image study by accessing the knowledge database; and configuring future clinical image study based on the determined configuration settings.

17. A data and study management system comprising:

a first management system including a knowledge database for storing data, the first management system being configured to, gather and store data correlated to at least a first clinical study, the first clinical study being an image-based study with a plurality of images being acquired by a plurality of imaging modalities, wherein the gathered data includes image data, metadata and image study results, the metadata being associated with the image data and containing configuration settings of at least one of the imaging modalities, the configuration settings being settings of the imaging modalities utilized when acquiring the associated image data during the first clinical study, correlate the image study results to the configuration settings of the imaging modalities, and determine optimum configuration settings for imaging modalities to be used in a future clinical study based on the gathered and stored data by accessing the knowledge database, the optimum configuration settings being usable in configuring the at least one second clinical study, which is subsequent to the first clinical study.

\* \* \* \* \*